(12) United States Patent
Jennings

(10) Patent No.: US 9,028,453 B2
(45) Date of Patent: May 12, 2015

(54) REUSABLE AUTO-INJECTOR

(75) Inventor: Douglas Ivan Jennings, Royston (GB)

(73) Assignee: Cilag GmbH International, Landis & Gyrstrasse (CH)

(*) Notice: Subject to any disclaimer, the term of this patent is extended or adjusted under 35 U.S.C. 154(b) by 841 days.

(21) Appl. No.: 12/997,593

(22) PCT Filed: Jun. 10, 2009

(86) PCT No.: PCT/GB2009/001448
§ 371 (c)(1),
(2), (4) Date: Dec. 11, 2010

(87) PCT Pub. No.: WO2009/153543
PCT Pub. Date: Dec. 23, 2009

(65) Prior Publication Data
US 2011/0098657 A1    Apr. 28, 2011

(30) Foreign Application Priority Data

Jun. 19, 2008 (GB) .................................. 0811346.6

(51) Int. Cl.
*A61M 5/32* (2006.01)
*A61M 5/24* (2006.01)
*A61M 5/28* (2006.01)
(Continued)

(52) U.S. Cl.
CPC ............. *A61M 5/2033* (2013.01); *A61M 5/204* (2013.01); *A61M 2005/3114* (2013.01); *A61J 1/2096* (2013.01); *A61J 2001/2013* (2013.01); *A61M 5/1782* (2013.01); *A61M 5/31511* (2013.01); *A61M 5/3202* (2013.01); *A61M 2005/206* (2013.01)

(58) Field of Classification Search
CPC . A61M 5/2033; A61M 5/204; A61M 5/1782; A61M 5/31511; A61M 5/3202; A61M 2005/206; A61M 2005/3114; A61J 1/2096
USPC ......... 604/110, 181, 187, 198, 200, 201, 205, 604/207, 218, 232, 407, 411, 412, 413, 414, 604/415; 141/2, 18, 22, 27
See application file for complete search history.

(56) References Cited

U.S. PATENT DOCUMENTS 1,845,036 A    2/1932   Busher
2,019,382 A   10/1935   Aronson
(Continued)

FOREIGN PATENT DOCUMENTS

CH         518102 A     1/1972
CN       2059579 U     7/1990
(Continued)

OTHER PUBLICATIONS

Austrian Search Report dated Jan. 22, 2006; Application No. 200608166-5.
(Continued)

*Primary Examiner* — Andrew Gilbert

(57) ABSTRACT

An injection device comprises a first sub-assembly. The first sub-assembly comprises a chamber for holding a fluid. The chamber comprises an inner surface and an exit aperture. The first sub-assembly comprises a stopper movably disposed within the chamber and having an outer surface substantially in contact with the inner surface about its perimeter. The first sub-assembly comprises an adapter adapted to transfer fluid into the chamber.

11 Claims, 8 Drawing Sheets

(51) Int. Cl.
*A61M 5/20* (2006.01)
*A61J 1/20* (2006.01)
*A61M 5/178* (2006.01)
*A61M 5/31* (2006.01)
*A61M 5/315* (2006.01)

(56) References Cited

U.S. PATENT DOCUMENTS

| | | |
|---|---|---|
| 2,531,267 A | 11/1950 | Harisch |
| 2,764,977 A | 10/1956 | Ferguson |
| 2,828,742 A | 4/1958 | Ashkenaz |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A * | 10/1996 | Meyer ............................ 604/82 |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A * | 7/2000 | Hager et al. ............... 604/131 |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |

(56) References Cited

U.S. PATENT DOCUMENTS

| | | |
|---|---|---|
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 * | 8/2003 | Knauer ............... 604/131 |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,344 B2 * | 12/2009 | Tennican et al. ............... 604/88 |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,736,353 B2 * | 6/2010 | Reynolds ............... 604/414 |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 * | 10/2010 | Moberg et al. ............... 604/201 |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 * | 1/2012 | Reynolds et al. ............. 141/329 |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,491,530 B2 | 7/2013 | Maritan |
| 8,696,628 B2 | 4/2014 | Grunhut |
| 2001/0005781 A1 | 6/2001 | Bergens et al. |
| 2001/0021828 A1 | 9/2001 | Fischer et al. |
| 2001/0037087 A1 * | 11/2001 | Knauer ............... 604/137 |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |

(56) References Cited

U.S. PATENT DOCUMENTS

| | | |
|---|---|---|
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1* | 4/2006 | Tennican et al. ............... 604/88 |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1* | 8/2006 | Reynolds ............... 604/220 |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172001 A1* | 7/2008 | Reynolds et al. ............. 604/232 |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1* | 2/2010 | Drake et al. ............... 604/135 |
| 2011/0092954 A1* | 4/2011 | Jennings ............... 604/506 |
| 2011/0098647 A1* | 4/2011 | Jennings ............... 604/154 |
| 2011/0098655 A1 | 4/2011 | Jennings et al. |
| 2011/0130743 A1* | 6/2011 | Jennings et al. ............. 604/506 |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |

(56) References Cited

FOREIGN PATENT DOCUMENTS

| | | |
|---|---|---|
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 59-115053 A | 7/1984 |
| JP | 2-185261 A | 7/1990 |
| JP | 2-502971 T | 9/1990 |
| JP | H02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |

(56) References Cited

FOREIGN PATENT DOCUMENTS

| | | |
|---|---|---|
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | 03/015846 A2 | 2/2003 |
| WO | WO 03/013632 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/047200 A1 | 4/2007 |
| WO | WO 2007/051330 A1 | 5/2007 |
| WO | WO 2007/066152 A | 6/2007 |
| WO | 2007/129324 A2 | 11/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |
| WO | 2010/023303 A1 | 3/2010 |

OTHER PUBLICATIONS

Australian Search Report dated Dec. 11, 2007; Application No. 200608165-7.
International Search Report dated Jun. 27, 2006; International Application No. PCT/GB2006/001023.
Great Britain Search Report dated Nov. 12, 2007; Application No. GB0715457.8.
European Search Report dated Aug. 3, 2011; Application No. 11170040.
European Search Report dated Aug. 3, 2011; Application No. 11163779.9.
International Search Report dated Sep. 5, 2005; International Application No. PCT/GB2005/002117.
Singapore Search Report dated Mar. 15, 2012; Application No. SG 201007017-5.
International Search Report dated May 30, 2006; International Application No. PCT/GB2005/003725.
European Search Report dated Aug. 3, 2011; Application No. 11170040.7.
Australian Search Report dated Dec. 6, 2007; Application No. SG 200608164-0.
International Search Report dated Sep. 9, 2005; International Application No. PCT/GB2005/002126.
European Search Report dated Jul. 20, 2011; Application No. 11163762.5.
Austrian Search Report dated Nov. 5, 2008; Application No. 200608166-5.
International Search Report dated Sep. 5, 2005; International Application No. PCT/GB2005/002131.
International Search Report dated Sep. 9, 2005; International Application No. PCT/GB2005/002120.
Australian Search Report dated Feb. 26, 2008; Application No. SG 200608071-7.
International Search Report dated Sep. 5, 2005; International Application No. PCT/GB2005/002137.
European Search Report dated Apr. 23, 2007; Application No. 06077332.2.
European Search Report dated Feb. 28, 2011; Application No. 10179733.0.
European Search Report dated Mar. 4, 2011; Application No. 10179736.3.
International Search Report dated Sep. 6, 2005; International Application No. PCT/GB2005/002108.
European Search Report dated Jun. 16, 2011; Application No. 11160134.0.
Singapore Search Report dated Feb. 26, 2008; Application No. 200608070-9.
International Search Report dated Sep. 5, 2005; International Application No. PCT/GB2005/002105.
International Search Report dated Sep. 5, 2005; International Application No. PCT/GB2005/002116.
Australian Search Report dated Dec. 5, 2007; International Application No. SG-200608165-7.
International Search Report dated Sep. 5, 2005; International Application No. PCT/GB2005/002128.
International Search Report dated May 23, 2006; International Application No. PCT/GB2006/001017.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
International Search Report dated May 29, 2006; International Application No. PCT/GB2006/001018.

(56) References Cited

OTHER PUBLICATIONS

International Search Report dated Jun. 2, 2006; International Application No. PCT/GB2006/001030.
European Search Report dated Aug. 4, 2011; Application No. 11169691.0.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
European Search Report dated Feb. 1, 2006; Application No. 05255298.1.
International Search Report dated Feb. 27, 2007; International Application No. PCT/IB2006/002792.
Great Britain Search Report dated Sep. 22, 2006; Application No. GB0610860.9.
International Search Report dated Aug. 22, 2007; International Application No. PCT/GB2007/001992.
Great Britain Search Report dated Sep. 28, 2006; Application No. GB0610859.1.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
Great Britain Search Report dated Sep. 29, 2006; Application No. GB0610856.7.
International Search Report dated Sep. 13, 2007; International Application No. PCT/GB2007/001999.
Great Britain Search Report dated Sep. 19, 2006; Application No. GB0610861.7.
International Search Report dated Aug. 28, 2007; International Application No. PCT/GB2007/001969.
Great Britain Search Report dated Nov. 12, 2007; Application No. GB0715460.2.
International Search Report dated Oct. 10, 2008; International Application No. PCT/GB2008/002578.
Great Britain Search Report dated Nov. 12, 2007; Application No. GB0715459.4.
International Search Report dated Oct. 14, 2008; International Application No. PCT/GB2008/002580.
Great Britain Search Report dated Nov. 12, 2007; Application No. GB0715461.0.
International Search Report dated Nov. 27, 2008; International Application No. PCT/GB2008/002579.
Great Britain Search Report dated Nov. 12, 2007; Application No. GB0715456.0.
International Search Report dated Oct. 10, 2008; International Application No. PCT/GB2008/002573.
Great Britain Search Report dated Nov. 8, 2007; Application No. GB0715457.8.
International Search Report dated Oct. 10, 2008; International Application No. PCT/GB2008/002583.
Great Britain Search Report dated Sep. 25, 2008; Application No. GB0811348.2.
International Search Report dated Sep. 30, 2009; International Application No. PCT/GB2009/001447.
European Search Report dated Oct. 15, 2013; Application No. 12182553.3.
Great Britain Search Report dated Sep. 25, 2008; Application No. GB0811346.6.
International Search Report dated Oct. 2, 2009; International Application No. PCT/GB2009/001448.
Great Britain Search Report dated Sep. 25, 2008; Application No. GB0811347.4.
International Search Report dated Oct. 5, 2009; International Application No. PCT/GB2009/001451.
Great Britain Search Report dated Sep. 25, 2008; Application No. GB0811345.8.
International Search Report dated Oct. 6, 2009; International Application No. PCT/GB2009/001453.
Great Britain Search Report dated Sep. 25, 2008; Application No. GB0811349.0.
International Search Report dated Oct. 5, 2009; International Application No. PCT/GB2009/001445.
Great Britain Search Report dated Sep. 25, 2008; Application No. GB0811343.3.
International Search Report dated Jan. 22, 2010; International Application No. PCT/GB2009/001446.
Great Britain Search Report dated Nov. 16, 2007; Application No. GB0716774.5.
International Search Report dated Jan. 12, 2008; International Application No. PCT/GB2008/002475.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
International Search Report dated Jan. 29, 2015; International Application No. PCT/EP2014/062167

* cited by examiner

REUSABLE AUTO-INJECTOR

FIELD OF THE INVENTION

This invention relates to an injection device, for example, a re-useable auto-injector into which a drug may be transferred from a vial prior to subcutaneous injection into a patient.

BACKGROUND OF THE INVENTION

The use of automatic injection devices (commonly known as auto-injectors) to deliver a medicament to a patient has provided many benefits over manual syringes. In particular, auto-injectors have helped to relieve the burden on hospital staff to deliver a drug to a patient because patients are able to use the devices on themselves reliably and safely and in their own home.

Known auto-injectors are described in WO 95/35126 and EP-A-0 516 473. These and similar auto-injectors are typically provided primed (i.e. pre-sprung) and ready to be used for injecting a patient. For these reasons, it is difficult to insert a drug into the auto-injector and, as a consequence, manufacturers of such auto-injectors have typically provided a pre-filled syringe for use in the auto-injector, or a complete auto-injector unit which is pre-filled with a particular drug.

This requires a more complicated and expensive manufacturing process than would be otherwise required for an auto-injector because manufacturers must also obtain and provide the drugs and maintain the facilities for storing and handling them. Furthermore, the manufacturer must operate separate production lines for each drug which is required.

Drugs for medical use are often manufactured and distributed in standard vials. In this way, drugs may be supplied in bulk conveniently and relatively cheaply, regardless of the way in which the drug is finally used.

A significant cost-saving could be made in providing an auto-injector device which is capable of drawing a drug from a standard vial rather than relying on a pre-filled syringe. Not only would such a device benefit the manufacturers, who would no longer have to provide bespoke drug-filled devices, but also hospitals, which would enjoy a simplified inventory system and could make use of the standard vials which are used on a regular basis, and patients, who could be provided with a supply of vials for self administration.

In addition, the use of vials permits the possibility of reusing a greater proportion of an auto-injector device. Typically, auto-injectors are provided in two subassemblies. The first subassembly comprises the operating mechanisms and all other reusable components and the second subassembly contains the injection components that must be replaced each time the device is used.

A major factor in the cost of the second subassembly is the provision of a chamber which is pre-filled with a drug to be injected. As explained above, providing a range of syringes is an expensive and time-consuming aspect of the manufacturing process of an auto-injector. The use of standard vials would enable this cost to be reduced.

SUMMARY OF THE INVENTION

The present invention aims to solve the aforementioned problems. Accordingly, an injection device comprises a first sub-assembly comprising a chamber for holding a fluid, said chamber comprising an inner surface and an exit aperture; a stopper movably disposed within the chamber and having an outer surface substantially in contact with the inner surface about its perimeter; and an adapter adapted to transfer fluid into the chamber.

Providing an injection device, such as an auto-injector, having a chamber into which a fluid may be transferred by a bespoke adapter has at least two benefits over the prior art. Firstly, manufacturers of auto-injector devices need no longer manufacture a range of pre-filled syringes to be inserted into a reusable sub-assembly. Rather, the manufacturer may provide instead a single type of sub-assembly in accordance with the present invention into which any variety of drug may be transferred immediately prior to injection. The single type of sub-assembly may be manufactured in bulk, thereby reducing the manufacturing costs.

This advantage leads on to a second benefit whereby the invention may be used in conjunction with any type of container from which a drug may be transferred into the chamber. In particular the invention may be used with standard vials.

Furthermore, the invention allows a greater proportion of the needle assembly to be reused. Whereas known auto-injector systems require pre-filled syringes, the capability of transferring fluid into a chamber within the needle device permits greater scope for reusability.

The adapter may comprise means for moving the stopper through the chamber; and means for transferring fluid into the chamber when the stopper is moved away from the exit aperture. The stopper may be provided at the distal end of the adapter.

Providing an adapter has the additional benefit of removing the need to disassemble the auto-injector to provide fluid directly into the chamber from which it is injected. An adapter which is configured to transfer fluid into the chamber enables a user to provide a fluid to be injected at a convenient location.

In the embodiments set out above, the volume of the chamber into which the fluid is transferred is defined by the space between the stopper and the exit aperture. Consequently, the volume is increased as the stopper is moved away from the exit aperture. The increase in volume causes a decrease in pressure in the chamber which thereby draws the fluid into the chamber. Of course, in alternative embodiments, an increase in chamber volume, and a corresponding effect, may be achieved by moving a stopper toward the exit aperture. Other embodiments which achieve an increase in chamber volume to draw fluid into the chamber are also envisaged.

Preferably, the stopper is adapted to transfer fluid into the chamber when the transfer assembly is moved with respect to the chamber away from the exit aperture.

The adapter may be adapted to receive a fluid container and transfer the fluid from the container to the chamber. Suitable containers may include any container configured to contain a drug and interface in some manner with the adapter. Thus, a standard vial used to contain and transport fluid medicaments may be used in combination with this invention. In this manner, the cost of providing an auto-injector system is greatly reduced as the process of transferring the drug into a syringe may be performed entirely by the patient, and standard vials are easy to obtain and low in cost. The container may be provided at the proximal end of the adapter.

It will be appreciated that the convenience of providing a fluid container such as a vial in communication with the adapter renders the transfer of fluid into the chamber particularly straightforward. In some embodiments, the adapter may extend outside of the injection device such that the fluid container may simply be pushed onto the adapter to create a fluid conduit between the container and the chamber.

In some embodiments, the means for transferring fluid into the chamber may comprise a hollow fluid transfer needle adapted to engage the fluid container to transfer fluid from the fluid container through the hollow needle, as the stopper is moved away from the exit aperture. Alternatively, the needle may comprise a fluid passageway including a unidirectional valve. This would enable transfer into, but not out of, the chamber.

Typically, containers used to contain drugs are provided with piercable foil or rubber caps. A needle, provided on the adaptor and configured to pierce the cap, may form part of the fluid conduit between the container and the chamber. Of course, a needle is merely preferred. Other means may be provided according to the particular configuration of the container. For example, if the container were to comprise a valve, the means for transferring fluid into the chamber may comprise a hollow passage connected to the valve by a fluid tight seal. Other embodiments comprising a means for transferring fluid from the container are also envisaged.

The hollow needle may be adapted to pierce the stopper to deliver fluid through the stopper into the chamber. In such an embodiment, the hollow needle may extend for the length of the adapter—from the container, at the proximal end, to the chamber, at the distal end—to provide a complete fluid conduit there-between. An additional benefit of this embodiment is that the force of engaging a container with the hollow needle at the proximal end may also be transferable through the hollow needle and thus sufficient to pierce the stopper at the distal end.

Alternatively, in place of such a needle, the adapter may comprise a separate second needle, adapted to pierce the stopper to permit fluid to be transferred into the chamber. In such an embodiment, it may be necessary to provide a means for driving the second needle through the stopper. Of course, the second needle may be substituted for a tube or similar means for transferring fluid. Such means may comprise a valve to permit fluid to be transferred into but not out of the chamber.

In preferred embodiments, the adapter comprises a fluid pathway to transfer fluid from the container to the chamber. In the case where the adaptor comprises a single hollow needle extending the length of the adaptor, the fluid pathway is through the needle. However, in the case where there is no such single conduit, the adaptor may provide a fluid pathway between the container and the chamber to transfer the fluid. The pathway may be a hollow passage or a tube, for example.

In an alternative embodiment, the auto-injector comprises a second sub-assembly comprising a releasable drive mechanism. The mechanism may comprise an elongate drive shaft which is driven against the stopper upon activation of the drive mechanism. As will be appreciated, in addition to its role in transferring fluid into the chamber, the stopper may also assist in performing the function of ejecting the fluid from the injection device into the patient.

The first sub-assembly may be detachable from the second sub-assembly. This is of particular benefit if the second sub-assembly is reusable. As explained above, in providing two detachable sub-assemblies, the second sub-assembly, comprising the drive mechanisms of the auto-injector may be reused, whereas the first sub-assembly, having been brought into contact with a drug and the patient, may be disposed of.

Of course, due to the nature of the invention, the first sub-assembly may also be reused if required. Following the expulsion of a drug into the patient, further fluid may be transferred into the first sub-assembly for injection into the same patient, as described above. This would reduce the long term cost of the auto-injector still further, as the only components requiring replacement would be the vial and the drug. In such circumstances, it may be advantageous to sterilise the first sub-assembly to prevent contamination.

In embodiments comprising a second sub-assembly, the adapter may be configured to be inserted within the elongate drive shaft to provide the fluid pathway. Thus, the elongate drive shaft may perform its function of driving the stopper to eject the fluid from the injection device, whilst the adapter may provide a fluid conduit to the stopper such that a fluid may be transferred into the chamber.

Optionally, the adapter is removably attachable to the stopper. Whereas the stopper must remain functional inside the auto-injector once the fluid has been transferred into the chamber, the adapter may have no further purpose. Thus it may be advantageous to remove the adapter from the stopper prior to injection. The adapter and the stopper may comprise inter-engagable threads to permit such a removable attachment. Of course, other removable engagement means, such as clips or detents, may be used instead.

BRIEF DESCRIPTION OF THE DRAWINGS

The invention will now be described by way of example with reference to the accompanying drawings, in which.

DETAILED DESCRIPTION OF THE DRAWINGS

Figure 1:
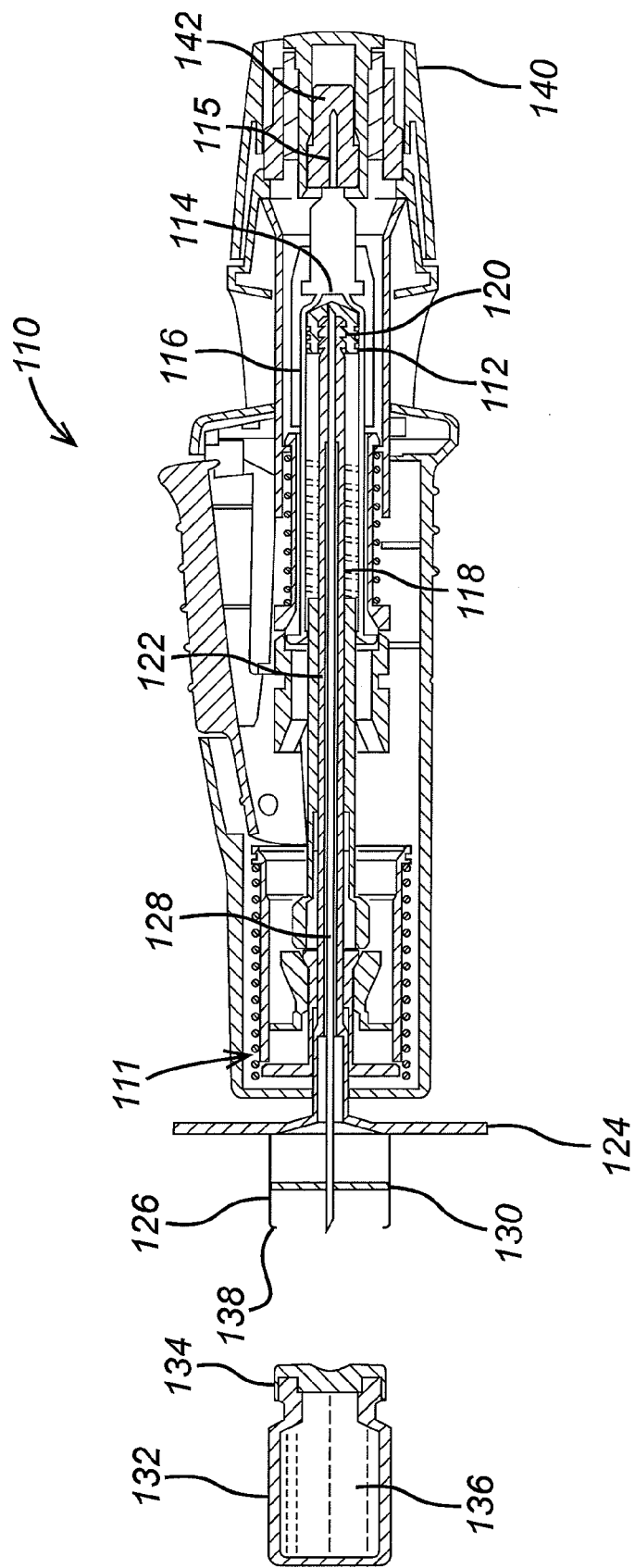
FIG. 1 is a side view of an auto-injector according to a first embodiment.

FIGS. 1 to 5 illustrate an auto-injector 110 according to a first embodiment of the present invention.

The auto-injector 110 comprises a drive means 111 coupled to a plunger disposed within a syringe. The plunger comprises a stopper 112 disposed within a chamber 116 having an inner surface. The stopper 112 is movable within the chamber 116 and has an outer surface which is substantially in contact with the inner surface about its periphery. The stopper is made from a pliable material. In the embodiment, the material is rubber, but other pliable materials may also be used. The contact between the stopper and the chamber forms a fluid tight and air tight seal.

At the distal end of the chamber 116 there is provided an exit aperture 114 in communication with an injection needle 115. When the auto-injector is primed and ready to inject a medicament into a patient, the operation of the device is as follows. Upon activation, the drive means 111 is configured to expose the injection needle 115 outside the casing of the auto-injector 110 and subsequently move the plunger 112 within the chamber 116 towards the exit aperture 114 to expel the contents of the chamber 116 through the exit aperture 114.

The auto-injector comprises a removable cap 140 including a sheath 142 disposed over the injection needle 115. The sheath 142 protects the injection needle 115 and provides a substantially fluid tight and air tight seal over the tip of the injection needle 115, to prevent fluid ingress or egress or other contamination.

Figure 2:
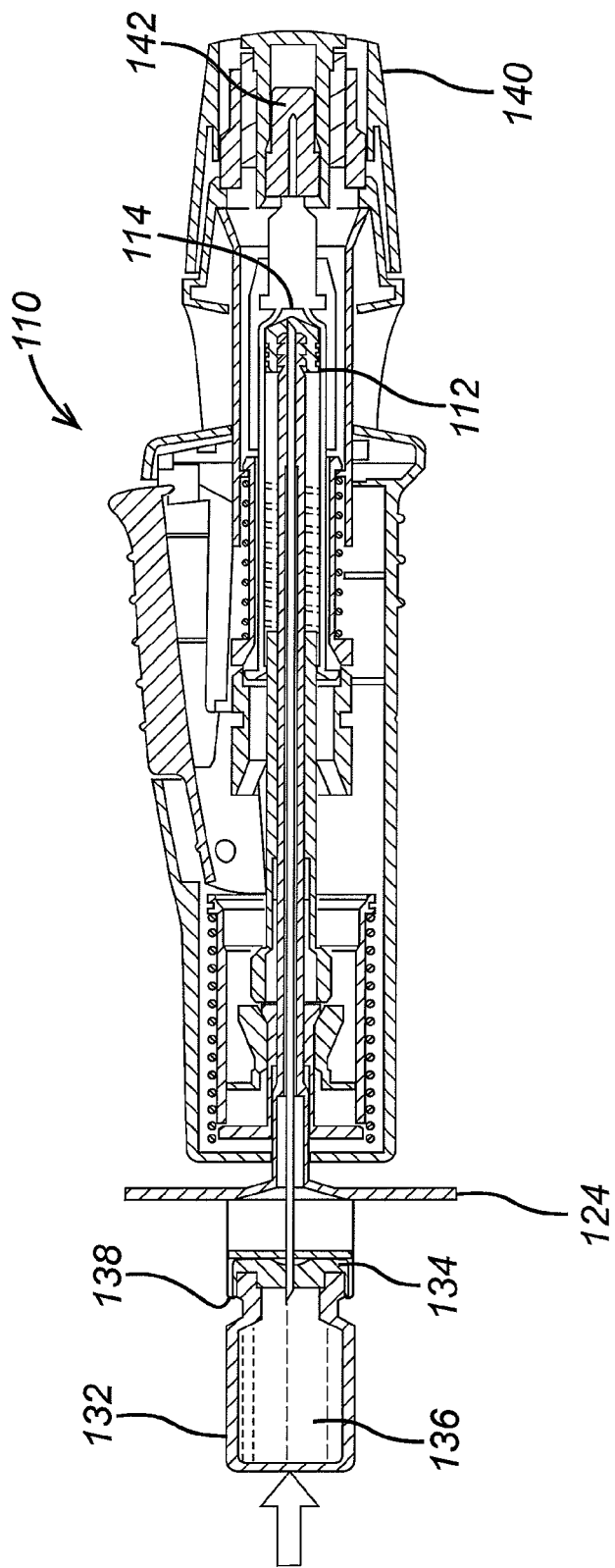
FIG. 2 is a side view of the first embodiment wherein a vial has been engaged with an adapter of the auto-injector.
Figure 3:
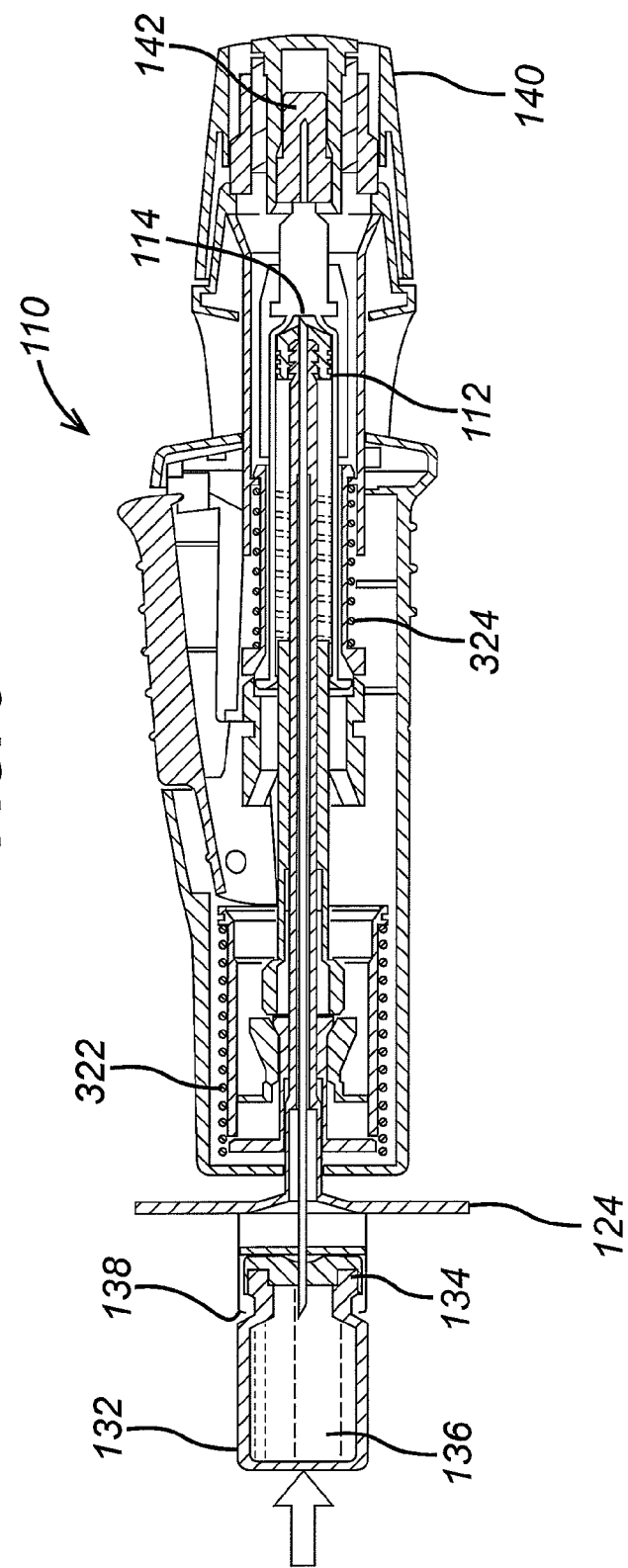
FIG. 3 is a side view of the first embodiment wherein a vial has been further engaged with an adapter of the auto-injector.

In the auto-injector of FIGS. 1 to 3, the stopper 112 abuts the exit aperture 114. The available volume of the chamber 116 into which a fluid may be transferred is minimal and, accordingly, the chamber 116 is substantially empty. When the stopper 112 is positioned away from the exit aperture 114 (see FIGS. 4 and 5), the available volume of the chamber 116 is at or substantially at its greatest. As shown, the chamber 116 is suitable for holding a fluid and, immediately prior to injection, contains a drug to be injected.

Referring to FIG. 1 in more detail, the auto-injector comprises an adapter 118 removably attached to the stopper 112.

The adapter 118 can be: provided in a kit which includes the auto-injector 110 and a vial 132 of drug to be administered (see below), provided preinstalled in the auto-injector 110, or provided separately for insertion into the auto-injector 110 by a user.

The adapter 118 and the stopper 112 comprise interconnecting threads 120 such that the adapter 118 may be removed from the stopper 116 by unscrewing the adapter 118. The adapter comprises an elongate shaft 122 having proximal and distal ends. The stopper 112 is attached to the adapter 118 at the distal end of the elongate shaft 122. At the proximal end of the adapter 118 is a handle 124. Disposed at the handle 124 is a port 126 configured to receive a vial 132 having a cap 134. The handle 124 is attached to the elongate shaft and enables a user to move the adaptor 118 within the auto-injector, thereby moving the stopper 112 within the chamber 116.

The adapter 118 further comprises a hollow needle 128 which extends through, and is moveable longitudinally within, the shaft 122. The needle 128 has proximal and distal ends corresponding to the proximal and distal ends of the shaft 122. At the proximal end, the needle 128 extends into the port 126. Fixed to the needle 128 at its proximal end is a grip 130. The grip 130 is moveable within the port 126, in conjunction with the needle 128. At its distal end, the needle 128 is adjacent the stopper 112. The needle 128 is configured to be capable of piercing both the stopper 112, at the distal end, and the cap 134, at the proximal end, when a container is engaged with the adapter 118.

The vial 132 contains a drug 136 to be injected into the patient. As can be seen in FIG. 2, when the vial 132 is engaged with the port 126 to a first position wherein the proximal end of the needle pierces the cap 134 of the vial 132, thereby creating a fluid conduit between the vial 132 and the hollow needle 128. The port 126 comprises a detent 138 configured to secure the vial 132 in this position within the port 126 such that the cap 134 abuts the grip 130.

The vial 132 may be further engaged further within the port 126 to a second position, as shown in FIG. 3. In moving the vial 132 from the first position to the second position, the vial pushes on the grip 130 which moves within the port 126 towards the exit aperture 114. As the grip is attached to the needle, movement of the grip causes a corresponding movement of the needle. As the needle 128 moves towards the exit aperture 114, it pierces the stopper 112, thereby completing the fluid conduit from the vial 132 through the needle 128 to the chamber 116. At this stage, however, the fluid remains within the vial 132.

Figure 4:
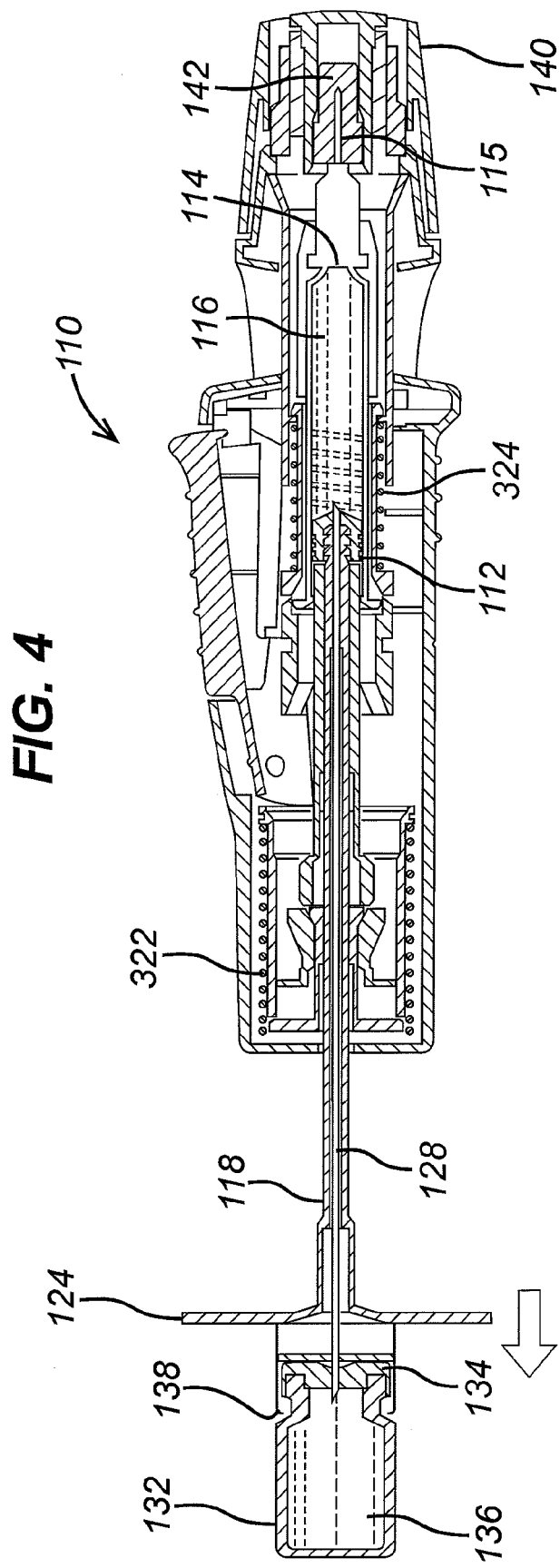
FIG. 4 is a side view of the first embodiment wherein a fluid has been drawn into the auto-injector.

FIG. 4 demonstrates the process of transferring the fluid from the vial 132 to the chamber 116. Once the needle 128 has pierced both the cap 134 and the stopper 112, a user may draw the adapter 118 through auto-injector, thereby drawing the stopper 112 through the chamber 116 away from the exit aperture 114.

As the stopper 112 moves away from the exit aperture 114, the available volume in the chamber 116 increases. As the injection needle 115 is sealed by the sheath 142 of the removable cap 140, thereby preventing ingress of fluid into the chamber 116 through the exit aperture 114, the pressure of that volume decreases and the pressure difference between the vial 132 and the chamber 116 causes fluid to be drawn from the vial 132, through the fluid transfer needle 128 and into the chamber 116.

Figure 5:
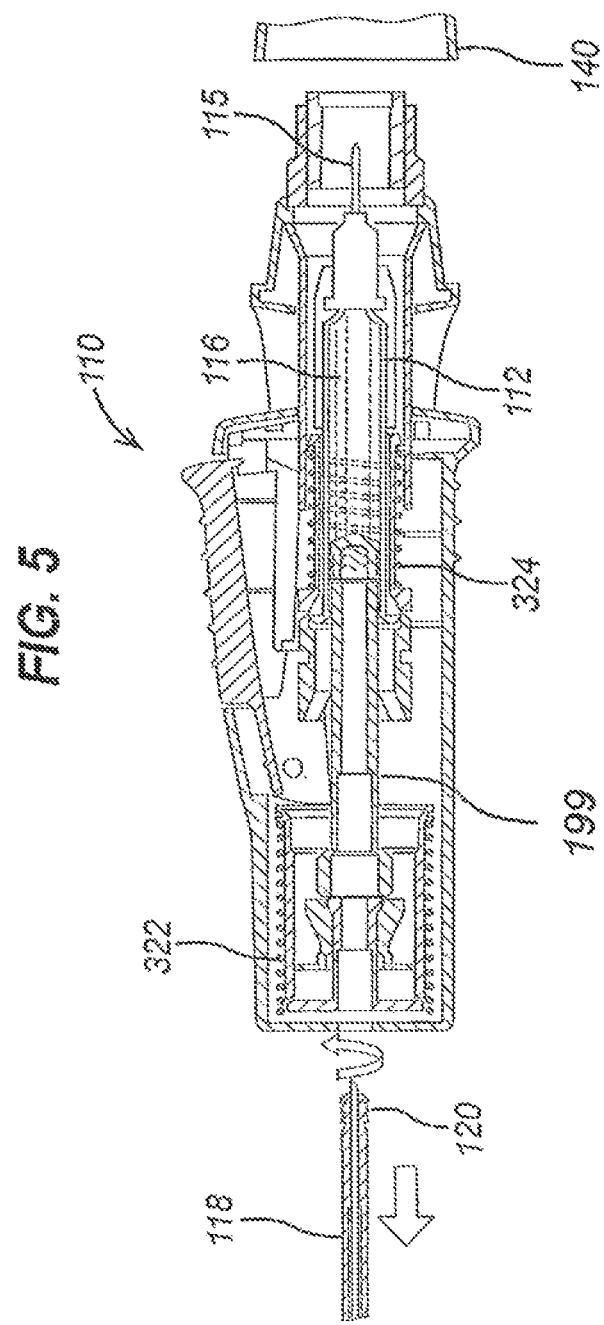
FIG. 5 is a side view of the first embodiment wherein the adapter has been removed from the auto-injector.

FIG. 5 illustrates the auto-injector after substantially all of the fluid from the vial 132 has been transferred into the chamber. The adapter 118 is removed from the stopper 112, and the adapter 118, along with the fluid transfer needle 128, is withdrawn from the auto-injector 110 through the elongate drive shaft 199. As the stopper is pliable, the aperture formed by the fluid transfer needle 128 is substantially sealed after the fluid transfer needle 128 is removed.

The auto-injector 110 now contains a drug to be administered.

Figure 6:
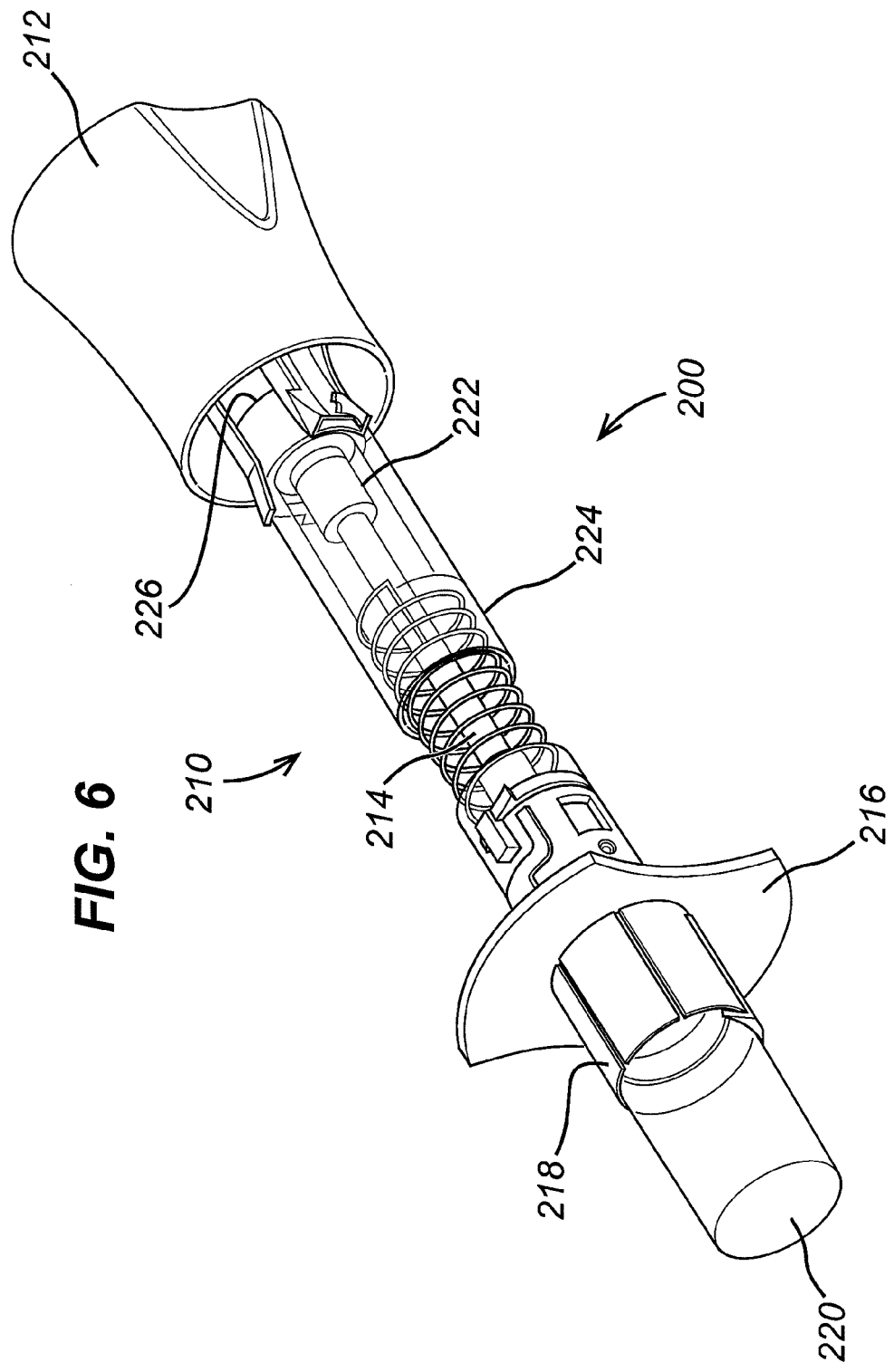
FIG. 6 is a side view of a first sub-assembly connected to an adapter in accordance with a second embodiment of the invention.
Figure 7:
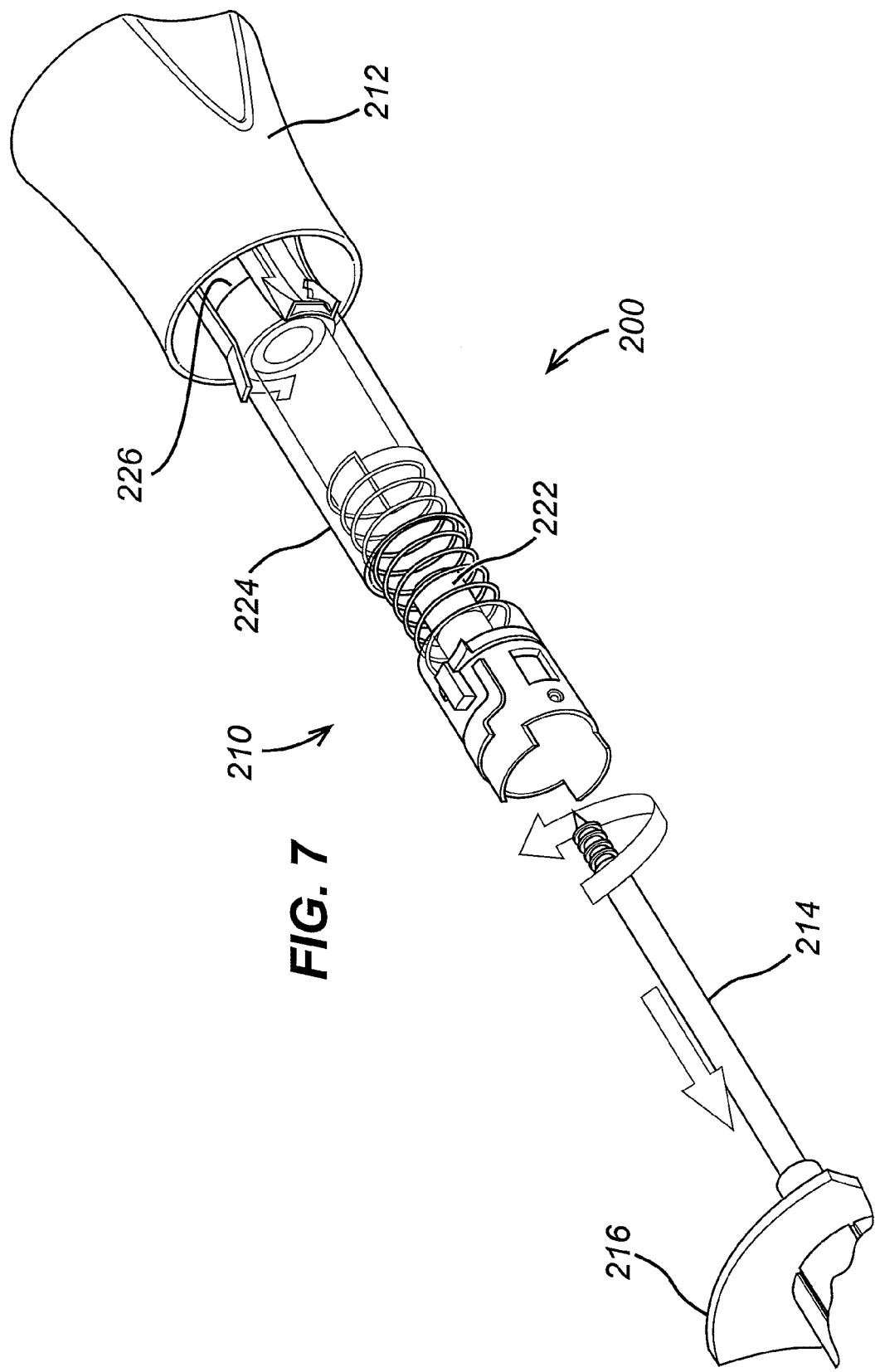
FIG. 7 is a side view of the second embodiment wherein a fluid has been drawn into the first sub-assembly and the adapter has been removed.
Figure 8:
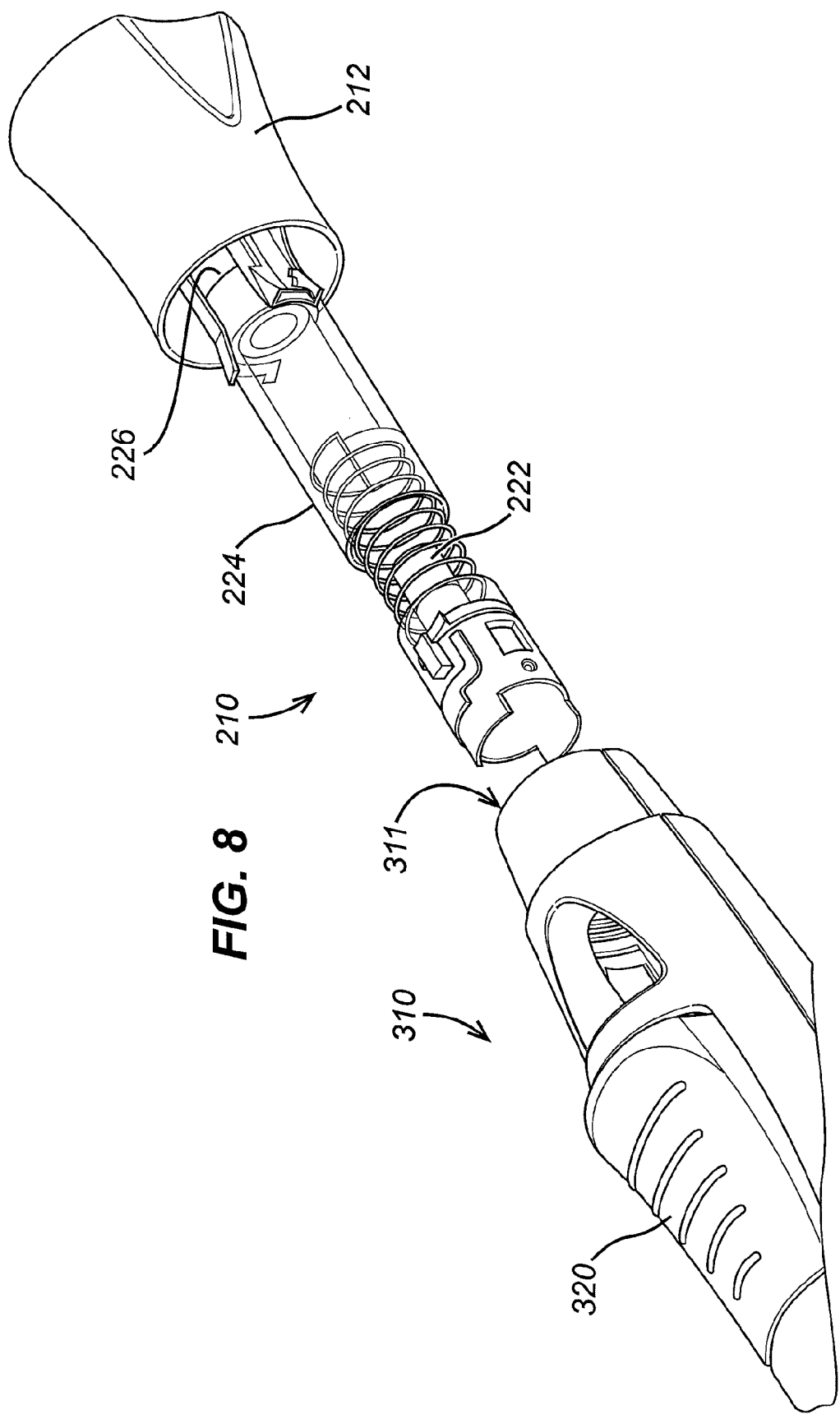
FIG. 8 is a side view of the second embodiment wherein the first sub-assembly in engaged with a second sub-assembly.

FIGS. 6 to 8 illustrate a kit 200 according to a second embodiment of the present invention.

FIG. 6 shows a first sub-assembly 210 suitable for use in an auto-injector. As with the first embodiment, the first sub-assembly 210 comprises a plunger disposed within a syringe. The plunger comprises a stopper 222 disposed within a chamber 224 having an inner surface. At the distal end of the chamber 224 there is provided an exit aperture 226 in communication with an injection needle (not shown). The stopper 222 and the chamber 224 are in accordance with the stopper and the chamber of the first embodiment.

The first sub-assembly comprises a removable cap 212 in accordance with the cap of the first embodiment. The first sub-assembly 210 also comprises an adapter 214 removably attached to the stopper 222. The adapter 214 is in accordance with the adapter of the first embodiment. The adapter comprises a handle 216 and a fluid transfer needle (not shown). Disposed at the handle 216 is a port 218 configured to receive a vial 220. The port 218 is in accordance with the port of the first embodiment.

As with the first embodiment, a user may engage the vial 220 with the port 218 such that the fluid transfer needle pierces the cap of the vial. Further engagement causes the fluid transfer needle to pierce the stopper 222 to create a fluid conduit from the vial 220 through the needle to the chamber 224.

As shown in FIG. 7, a user draws the adapter 214 through the first sub-assembly 210, thereby drawing the stopper 222 through the chamber 224 away from the exit aperture 226. As with the first embodiment, the available volume of the chamber 224 into which a fluid may be transferred increases as the stopper 222 is moved away from the exit aperture 226. As the volume increases, the pressure of that volume decreases, thereby drawing fluid from the vial through the needle into the chamber 224. Once the fluid has been transferred, the adapter is removed from the stopper 222 and the adapter, along with the fluid transfer needle, is withdrawn.

Referring now to FIG. 8, once the first sub-assembly 210 is primed, it is inserted into an open aperture 311 on a second sub-assembly 310. The second sub-assembly 310 comprises a drive mechanism which is configured to operate on the components of the first sub-assembly 210 as follows.

Once engaged, the first 210 and second 310 sub-assemblies form an injection device which is primed and ready to use in an identical state to the auto-injector 110 of the first embodiment when it has been filled with a drug. Indeed, the auto-injector 110 of the first embodiment comprises the first and second sub-assemblies 210, 310, but in the first embodiment, these sub-assemblies have been assembled prior to loading of the drug.

Thus, in both the first and second embodiments, activation of a release mechanism 320 of the second sub-assembly 310 releases a drive mechanism, in the form of drive spring 322 acting on the driving mechanism, to cause the needle to be exposed outside of the auto-injector to pierce the skin of a patient and the stopper 112 to be driven through the chamber 116 to inject the patient with the fluid. After all the fluid has been expelled, the needle is subsequently retracted by a retraction mechanism 324 so that it is wholly within the assembled auto-injector 110.

Once the fluid has been injected, the second sub-assembly 310 may be disassembled from the first sub-assembly 210 and reused. The first sub-assembly 210 may be discarded and a new first sub-assembly provided for subsequent injections, or may be sterilised for reuse.

It will be appreciated that modifications may be made to the embodiment described without departing from the scope of the invention, as defined in the appended claims.

The invention claimed is:

1. An auto-injector comprising:
   a first sub-assembly comprising:
      a chamber for holding a fluid, said chamber comprising an inner surface and an exit aperture;
      a stopper movably disposed within the chamber and having an outer surface substantially in contact with the inner surface about the stopper's outer perimeter; and
      an adapter adapted to transfer the fluid into the chamber, wherein the adapter is adapted to receive a fluid container and transfer the fluid via a fluid pathway from the fluid container to the chamber, wherein the adapter comprises:
         an elongate shaft to move the stopper through the chamber; and a hollow fluid transfer needle adapted to engage the fluid container to transfer the fluid from the fluid container through the hollow fluid transfer needle, as the stopper is moved away from the exit aperture;
         wherein the hollow fluid transfer needle is adapted to pierce the stopper to deliver the fluid through the stopper into the chamber; and
   a second sub-assembly comprising:
   a releasable drive mechanism, said releasable drive mechanism comprising an elongate drive shaft which is driven directly against the stopper upon activation of the releasable drive mechanism.

2. The auto-injector of claim 1, wherein the adapter is configured to be inserted within the elongate drive shaft.

3. The auto-injector of claim 1, wherein the adapter is removably attachable to the stopper.

4. The auto-injector of claim 3, wherein the adapter and the stopper comprise inter-engagable threads to permit removable attachment.

5. The auto-injector of claim 1, wherein the stopper is further adapted to expel the fluid held within the chamber when the stopper is moved toward the exit aperture.

6. The auto-injector of claim 1, further comprising an injection needle in fluid communication with the exit aperture.

7. The auto-injector of claim 6, wherein the releasable drive mechanism is, upon activation, adapted to:
   (a) move the chamber and the injection needle from a refracted position in which the injection needle is wholly inside a housing of the auto-injector to an extended position in which the injection needle is at least partially outside the housing; and
   (b) subsequently move the stopper within the chamber toward the exit aperture to expel the fluid out of the injection needle.

8. The auto-injector of claim 7, further comprising a retraction mechanism adapted to retract the injection needle into the housing after the fluid has been expelled.

9. The auto-injector of claim 1, claim 7 or claim 8, wherein:
   the first sub-assembly is detachable from the second sub-assembly; and
   the second sub-assembly is reusable.

10. An injection kit comprising:
    a first sub-assembly for an auto-injector comprising:
       a chamber for holding a fluid, said chamber comprising an inner surface and an exit aperture;
       a stopper movably disposed within the chamber and having an outer surface substantially in contact with the inner surface about the stopper's outer perimeter; and
       an adapter adapted to transfer the fluid into the chamber, wherein the adapter is adapted to receive a fluid container and transfer the fluid via a fluid pathway from the fluid container to the chamber, wherein the adapter comprises:
          an elongate shaft to move the stopper through the chamber; and
    a hollow fluid transfer needle adapted to engage the fluid container to transfer the fluid from the fluid container through the hollow fluid transfer needle, as the stopper is moved away from the exit aperture;
       wherein the hollow fluid transfer needle is adapted to pierce the stopper to deliver the fluid through the stopper into the chamber; and
    a second sub-assembly comprising:
    a releasable drive mechanism, said releasable drive mechanism comprising an elongate drive shaft which is driven directly against the stopper upon activation of the releasable drive mechanism.

11. The injection kit of claim 10, further comprising a vial of the fluid to be transferred for connection to the adapter.

* * * * *